Figure 1:
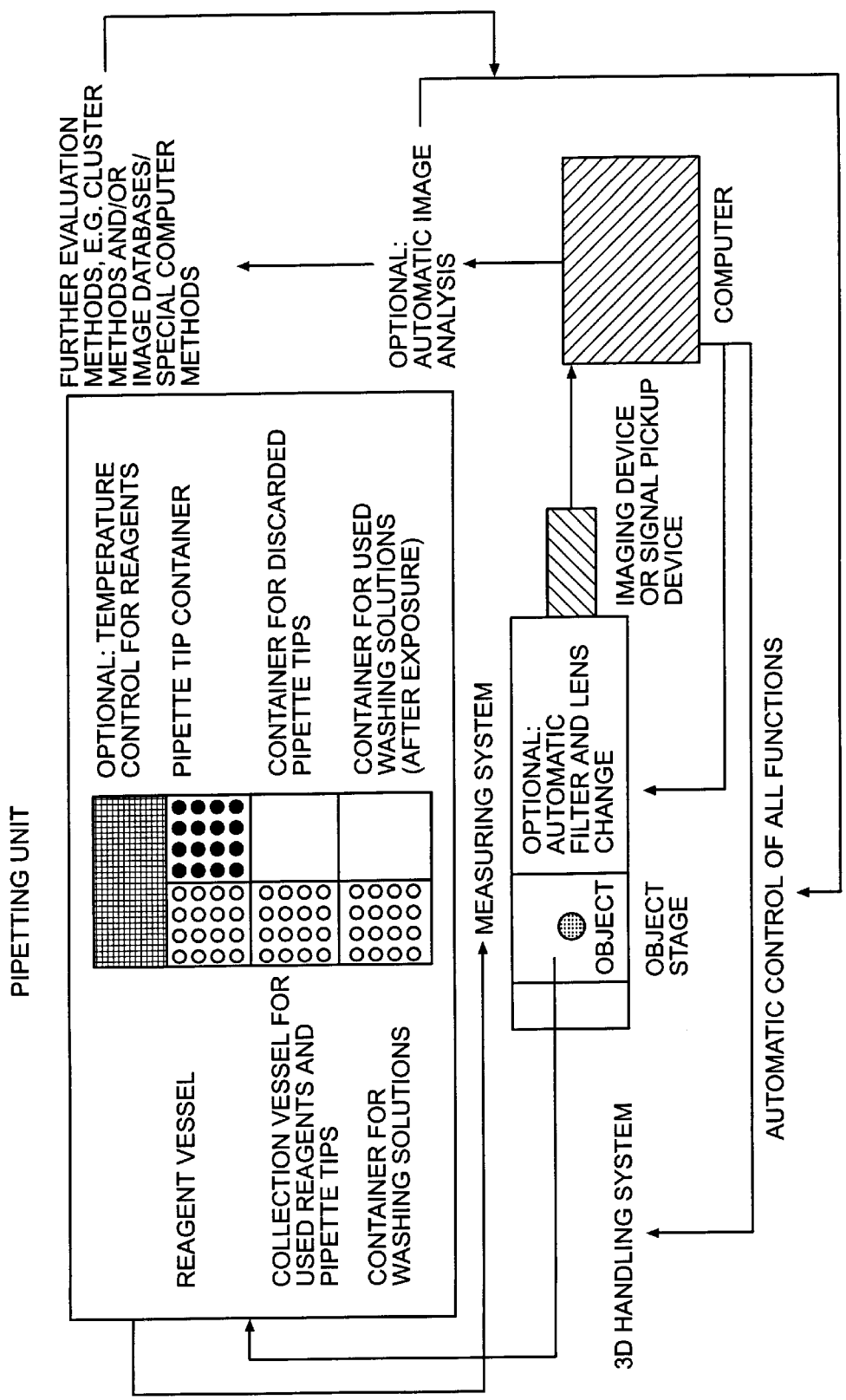

United States Patent [19]
Schubert

[11] Patent Number: 6,150,173
[45] Date of Patent: Nov. 21, 2000

[54] AUTOMATED DETERMINING AND MEASURING DEVICE AND METHOD

[76] Inventor: Walter Schubert, Am Muhlengrund 9, D-39175 Biederitz, Germany

[21] Appl. No.: 09/353,942

[22] Filed: Jul. 15, 1999

Related U.S. Application Data

[63] Continuation of application No. 08/858,374, May 19, 1997, abandoned.

[30] Foreign Application Priority Data

May 29, 1996 [DE] Germany ............................ 196 21 364
Mar. 7, 1997 [DE] Germany ............................ 197 09 348

[51] Int. Cl.$^7$ .................................................. G01N 35/00
[52] U.S. Cl. ................................ 436/43; 422/63; 422/65; 422/67; 422/68.1; 422/100; 422/82.08; 436/47; 436/48; 436/49; 436/50; 436/164; 436/172; 436/174; 436/180
[58] Field of Search .................................. 422/63, 65, 67, 422/68.1, 100, 82.08; 436/43, 47, 48, 49, 50, 164, 172, 174, 180

[56] References Cited

U.S. PATENT DOCUMENTS

| | | | |
|---|---|---|---|
| 4,265,855 | 5/1981 | Mandle et al. | 422/65 |
| 4,299,796 | 11/1981 | Esch | 422/63 |
| 4,772,453 | 9/1988 | Lisenbee | 422/52 |
| 4,816,418 | 3/1989 | Mack et al. | 436/518 |
| 4,931,402 | 6/1990 | Abplanalp | 435/291 |
| 5,096,670 | 3/1992 | Harris et al. | 422/65 |
| 5,104,621 | 4/1992 | Pfost et al. | 422/67 |
| 5,306,510 | 4/1994 | Meltzer | 422/65 |
| 5,589,351 | 12/1996 | Harootunian | 435/29 |
| 5,720,928 | 2/1998 | Schwartz | 422/186 |

FOREIGN PATENT DOCUMENTS

| | | |
|---|---|---|
| 0383322 | 8/1990 | European Pat. Off. . |
| 2903625C2 | 8/1979 | Germany . |
| 2903855A1 | 8/1980 | Germany . |
| 3346532A1 | 7/1984 | Germany . |
| 3642209A1 | 6/1987 | Germany . |
| 3836716A1 | 5/1990 | Germany . |
| 4011584A1 | 10/1990 | Germany . |
| 4113377A1 | 10/1991 | Germany . |
| 4110217C2 | 10/1992 | Germany . |
| 4211904A1 | 11/1992 | Germany . |
| 4214430A1 | 11/1992 | Germany . |
| 4313603C2 | 10/1993 | Germany . |
| 4404896A1 | 8/1994 | Germany . |
| 19709348C2 | 12/1997 | Germany . |

OTHER PUBLICATIONS

Confocal Spectral imaging analysis in studies of the spatial distribution of antiumour drugs within living cancer cells–Elsevier Science B.V. –1994.

*Primary Examiner*—Jill Warden
*Assistant Examiner*—Patricia Kathryn Bex
*Attorney, Agent, or Firm*—Womble Carlyle Sandridge & Rice

[57] ABSTRACT

The invention relates to an automated device for determining or identifying and measuring a random number of different molecular classes, molecular parts or molecular groups in liquid or solid objects, in particular in cells and tissue specimen, said device comprising a combination of a pipetting system, a 3D handling system and an optical measuring system, preferably a microscope stand including an imaging device.

The invention further relates to an automated method for determining or identifying and mapping a random number of molecular classes, molecular parts and molecular groups in objects, with which a random number of different reagent solutions may be applied simultaneously or sequentially to a liquid or solid object, in particular a cell, cells or a tissue specimen, and measured. An important field of application of the invention is cancer research as well as research into the immune system. Within a very short time, precise evaluation results as to quantity as well as quality are obtained concerning the arrangement and correlative distribution of the molecular species in the object under examination. These results may for example give an insight into various diseases and their treatment.

17 Claims, 1 Drawing Sheet

AUTOMATED DETERMINING AND MEASURING DEVICE AND METHOD

CROSS REFERENCE TO RELATED APPLICATIONS

This application is a continuation of application Ser. No. 08/858,374, filed on May 19, 1997, now abandoned, which application claims the benefit of German application no. DE19621364.9, filed May 29, 1996 and German application no. DE19709348.5, filed Mar. 7, 1997.

The present invention relates to an automated device for determining or identifying and measuring a random number $X_n$ (n=1,2,3, . . . N) of molecular classes, molecular parts or molecular groups in a liquid or solid object. The invention further relates to a method for determining or identifying and mapping a random number $X_n$ (n=1,2,3, . . . N) of molecular classes, molecular parts or molecular groups in a liquid or solid object, in which a random number of reagents is automatically applied to an object simultaneously or sequentially and measured.

Various techniques and methods are used in the natural sciences, in particular in biology, chemistry, biochemistry and medicine, to examine and determine or identify the correlative distribution and/or combination and arrangement of different molecular classes or molecular groups, for example of protein molecules or polymers, or, if necessary, the tinctorial behaviour of the object. These different methods and techniques are aimed at gaining knowledge about the arrangement, the distribution and the structure of the molecular groups in the respective liquid or solid objects. For this purpose, the objects to be examined are treated with specific solutions so as to examine and determine or identify the specific molecular classes or molecular groups for example based on the complexes formed (e.g. EDTA metal complexes or antigen/antibody complexes etc.). Such methods are predominantly used in the fields of medicine and biology in order to obtain diagnostic measurement data for certain disease symptoms based on the arrangement and distribution of such molecular species in the object in question or to gain an insight into the molecular organisation of cells or cell systems.

The manual methods of the prior art follow a certain scheme. In biology or medicine for instance, the object to be examined is treated with a solution containing a specific reagent. Such reagent may be a colorant, an antibody etc. which reacts with a certain molecular group, and particular to form a specific complex. This means that the specific reagent labels specific groups or sites in the object to be examined. After a certain exposure time the specifically labelled object is then examined, usually by means of signal distribution patterns, e.g. in the microscopic examination of cells by means of different fluorescent signals using fluorescein-isothio-cyanate or phycoerythrin.

According to the prior art, some of the manual methods, such as the dyeing of tissue sections using simple color solutions, may also be effected by special automatic dyeing devices; for simple molecular markings in cells, automatic labelling devices exist.

In either case—i.e. the manual and the automatic treatment of objects, in particular of cells or tissue sections, with reagents—the results need to be visually controlled and evaluated in a different and separate device specifically designed and provided for this purpose, after the object has been placed in such device, e.g. a microscope, by hand.

According to the prior art, more complex methods of treating objects with reagents, e.g. the sequential application of various solutions on cells, which need to be evaluated and recorded at certain times during this process, are entirely limited to manual methods and very susceptible to errors, i.e. they may neither be evaluated as to quantity nor may they be used in statistics. Where such methods require very precise time checks of the individual intermediate steps (e.g. in intervals of precisely 20 minutes each) over a long total time period, e.g. 34 hours, the limits of such methods being feasible for an examiner are exceeded by far.

For determining or identifying the correlative distribution of multiple molecular classes with regard to each other, biomedicine often uses various different fluorochromes which are each coupled (directly or indirectly) to the molecular classes to be localized. In this case the fluorescent signals emanating from these different fluorochromes are detected separately. Relating these signals to each other will eventually give information on the correlative distribution of the various molecular classes.

However, these methods, which are above all important for examining combinatorial molecular differentiation processes, are limited to the examination of a maximum of 4 to 5 different fluorescent signals in a given sample since it is impossible to separate a higher number of different fluorescent signals from each other. The methods existing so far are therefore very limited when it comes to determining or identifying and localizing the molecular classes present in one and the same sample. It has thus hitherto been impossible to detect higher order combinatorial order forms.

This limitation can be overcome by destroying—in a first step after certain molecular classes or molecular groups have been labelled in the above mentioned manner—the fluorochromes bound at the site of this labelling by bleaching due to UV irradiation.

Subsequently, a second or further solution is applied to the object which contains one and up to a maximum of 5 different fluorochromes for labelling further molecular classes. After the required exposure time, new specific signal distribution patterns are in turn obtained from the specifically labelled molecules. After bleaching the fluorochromes, this process is repeated a number of times. The number of signal distribution patterns thus increases with the number of reagent solutions used. These different signal distribution patterns may give an insight into the arrangement and distribution of the molecular groups in the object.

However, these known methods for determining or identifying molecular classes or molecular groups exhibit considerable shortcomings since the individual method steps are performed by hand. Performing these steps by hand is very time-consuming—which makes them too error prone or not sufficiently standardizable for modern methods which have to render exact evaluations as to quantity. One example is that the reagent solution is usually pipetted onto the object by hand, the object then being placed onto a microscope stage by hand and positioned appropriately. All further pipetting operations are then performed on the object by hand with the object remaining unchanged on the microscope stage. In manual pipetting operations the exact dosage of the reagent solution is not always precisely adhered to. In the case of repeated pipetting actions, it is likewise impossible to always place the pipette above precisely the same spot of the object. Moreover, it may easily happen that the pipette contacts the object to be examined so that the respective spot of the object may be changed. This will result in a distortion of evaluation results.

A test series comprising more than 20 different markers, which are used up manually in periods of 30 minutes each, takes several days to be completed. A subsequent evaluation of signals or images, i.e. the determination or identification of the correlative molecular distribution patterns, may also take several days up to weeks since the different signal distribution patterns will first have to be evaluated individually before they can be combined to give an overall image. This evaluation method is also very time-consuming. It may therefore take several weeks before an evaluation result is eventually obtained.

For these reasons, using the known methods, only as little as 4–5 molecular classes at the most may be localized and determined or identified in an object, i.e. the number of molecular classes or molecular groups which could be examined and determined or identified has so far been dry restricted.

For this reason, it is impossible at present to perform an exact quantitative microscopic examination of more complex molecular combination patterns of individual samples.

It is the object of the present invention to overcome the shortcomings or restrictions underlying conventional methods for determining or identifying molecular classes, molecular groups or molecular parts (e.g. epitopes, domains) in different objects.

The present invention thus relates to an automated device for determining or identifying and measuring a random number $X_n$ (n=1,2,3, ... n) of molecular classes, molecular groups and molecular parts inma liquid or solid object. Using this device, a random number of individual labelling patterns of one and the same object may be recorded and transformed into highly complex molecular combination patterns through computer-aided image superimposition.

A further subject-matter of the present invention is an automated method by means of which a random number X (X=1,2,3, ... N) of different molecular classes or molecular groups in a liquid or solid object may be determined or identified automatically.

In this automatic method, based on repeated fluorescence bleaching operations and by successively performing a random number of fluorescence labelling and fluorescence bleaching operations, random complex combinations of different molecular species and molecular classes in one and the same (preferably biological) structure may be determined or identified. In this way, higher forms of combinatorial order in systems, preferably biological ones, may be determined or identified.

The device according to the present invention comprises a pipetting system, 3D handling system as well as an optical measuring system. Especially preferred is the use of an inverse or upright microscope stand. The 3D handling system comprises a robot or a linear guiding system. A linear guiding system, and thus the entire linear array of a reagent rack, is not very complex from a technical point of view and is hence very economical. Furthermore, an imaging device is connected to the device and is in particular connected to the microscope unit. The device is automated, i.e. the functional operations of its components—both individually and in combination—are computer controlled and monitored.

The FIGURE shows the schematic structure of an embodiment of the device according to the invention.

Automatic pipetting devices are sufficiently known in the prior art. However, these are not suited for the device according to the present invention. For precisely detecting and mapping the different molecular classes, it must be possible to repeatedly position the pipette tip in exactly the same place of the liquid or solid object. Moreover, it is necessary or desirable to change the pipette tip automatically before a new solution is taken up in order to safeguard that the tip does not contain a minute amount of the solution previously used anymore. The pipetting system comprises a container for the solutions, a collection vessel for used solutions and pipette tips, a container for the washing solutions, a container for the pipette tips which may be used, a container for the used and discarded pipette tips and a container for the washing solutions after the exposure time. In addition, the pipetting unit may be provided with a temperature control means for the reagents stored therein.

The pipetting system of the device according to the invention exhibits adequate accuracy in repeatedly positioning the pipette in the object sample so that the pipette can be moved to a certain spot of the object a random number of times. Preferably, the accuracy in repeatedly positioning the pipette should be at least ±0.1 mm. Furthermore, the pipetting system is controlled such that both take-up and dispensing of each solution used occur automatically. The pipetting system has a high degree of movability and flexibility.

3D handling systems are used in almost all sectors of industry today. The 3D handling system of the present invention which introduces the pipette into the solution, moves the filled pipette to the object and resumes the starting position after the solution has been dispensed, must have an accuracy in repeatedly positioning the pipette which is adapted to the object. The accuracy of the 3D handling system in repeatedly positioning the pipette is particularly required for specifying certain spots or places in the objects which are treated with different solutions in the course of a test series in order to examine the specific molecular classes. The 3D handling system must be in a position to approach the spots of the object which have been pre-specified for the entire method a random number of times since deviations may result in distorted evaluation results. For this reason, it likewise exhibits an accuracy in repeatedly positioning the pipette which is preferably at least ±0.1 mm. The 3D handling system moves within a 3D working area and has a rotational axis for exactly positioning the pipetting device. The individual functions of the pipetting system and of the 3D handling system as well as the technical cooperation of both systems are computer controlled.

A further essential component of the automated device according to the invention is the optical measuring system, in particular a microscope. Particularly preferred is the use of an inverse or upright microscope stand. If required, the microscope may be equipped with a climatic box for maintaining exact physiological conditions for living cells, in particular for long-term experiments. The microscope stand has automatic filter and lens charge means.

The microscope stand is connected to an imaging device. This imaging device allows computer controlled image evaluation since it takes images of the respective signal distribution pattern optically transmitted via the microscope after every run.

The overall automated device of the present invention has the following technical parameters:

1. It can be controlled via a central computer
2. the pipette tips are changed automatically
3. the 3D handling system and the pipetting system exhibit an accuracy in repeatedly positioning the pipette which is preferably at least ±0.1 mm
4. the individual systems are not impaired by vibrations, emissions, fields and the user is not disturbed by noise
5. if necessary, a thermostat may be provided
6. a 3D working area and a rotational axis for exactly positioning the pipetting device must be given.

The automatic device according to the invention may be used in various application fields in the natural sciences, in particular in biology and in medicine. Especially important fields of application are research into and diagnostics of cancer and the immune system.

The method according to the invention for determining or identifying molecular classes or molecular groups in solid or liquid objects is characterized in that in a liquid or solid object a random number $Xn$ (n=1,2,3, . . . N) of different molecular classes or molecular groups may be determined or identified and mapped automatically a random number of times by means of specific reagent solutions $Yn$ (n=1,2,3, . . . N).

The method comprises the following automatic steps:

I. A reagent solution Y1 is automatically taken up from a container containing solution Y1 by the pipetting system.

II. Solution Y1 is automatically applied to the object (solid or liquid) which is mounted on a stage or an object-carrier.

III. Solution Y1 is left to react on the object for a certain, automatically specified time.

IV. Immediately following such exposure or, if necessary, also during the actual exposure, an image of the object which has been treated with solution Y1 may be taken by automatically actuating the imaging system of the microscope. As an alternative, step V may be made to precede step IV.

V. After solution Y1 has reacted on the object for a certain, automatically specified time, solution Y1 is removed (sucked off) by the pipetting system.

Depending on the object and the special determination or identification to be performed, different alternatives are possible in step VI.

VIa. A second solution Y1 or solution Y2 or a mixture of both Y1 and Y2 is applied by means of the pipetting system.

VIb. After removal of solution Y1, of solution Y2 or of a mixture of both Y1 and Y2, a washing solution Z1 is automatically applied to the object and left to react on the object for a period of time which can be specified.

VIc. Immediately following the removal of solution Y1, a washing solution Z2 or Z3 or Zn (n=1,2,3, . . . N) is automatically applied via the pipetting system.

VId. Immediately following the removal of solution Y1, the washing solutions Z1 to Zn are applied to the object in a specified order which may be varied.

VIe. After a variable automatically specified time following exposure to and removal of solution Y1, a washing solution is applied to the object.

VIf. Only after a variable certain specified time has elapsed, washing solution Z1 to Zn are automatically applied to the object in a certain order and for a certain exposure time.

VII. Steps I–VIf may be repeated a random number of times with one solution Y3 or with a random number of different solutions Yn or a mixture of said different solutions Yn.

Steps I–VII may be interrupted at any time and at random stages of the steps and may be repeated a random number of times, at least as long as this is possible with the object to be examined. The individual cycles may be carried out very fast, preferably within periods of 5 min to 30 min each.

This method of the invention can be performed with the automated device of the present invention which comprises a 3D handling system, a pipetting system, an optical measuring system, in particular a microscope stand, and an imaging device—all of which are automatically controlled by a computer.

The inventive method will render exact evaluation results as to quantity and quality within a certain time. Furthermore, a random number of molecular classes, molecular species or parts of molecules in an object may be examined and determined or identified. The error sources arising when the method is performed by hand have been largely eliminated. As a consequence, the automatic method of the present invention exhibits considerable advantages over prior art methods for examining and determining or identifying different molecular groups.

In a preferred embodiment of the present invention, the method is performed in order to automatically detect and map a random number of molecular species or epitopes in a cell or a tissue specimen, with the aim to obtain knowledge on the arrangement and the correlative distribution of the molecular groups in order to gain an insight into various diseases and their treatment. For this purpose, the cells or tissue specimens are treated with a first reagent solution Y1 which for example contains fluorescent antibodies or ligands. After a certain incubation period, special distribution patterns of labellings of the specifically labelled tissue specimens or cells are photographed and recorded.

For recording the distribution pattern of the labellings, a fluorochrome is automatically excited, for example under automatic computer control, and a shutter of the video camera is opened for a predetermined time. The fluorescence signal is thus recorded, preferably in the form of a digital signal, i.e. a digitalized image. After the predetermined opening time of the shutter, the shutter is closed again automatically, as is the shutter for the automatic fluorescence excitation. The same operation may be repeated automatically for different fluorochromes simultaneously present, i.e. bound, in the sample, using the appropriate fluorescence filters and shutter actuations.

The specifically labelled samples are subsequently bleached and washed and then treated with a second reagent solution Y2 or with a random number of reagent solutions Yn or mixtures thereof. The automatic method which can be performed by means of a random number of such labelling-imaging-bleaching cycles is particularly suitable for use in medicine and biology. As long as this is possible with the solid or liquid object to be examined, the individual steps may be repeated a random number of times. The first step and/or the subsequent steps or these repetitive cycles are carried out by means of an optical method such as fluorescence microscopy in combination with transmitted-light microscopy. The first run of the method is terminated by recording an image of the labelled tissue specimen or cell, e.g. a phase contrast image or a differential interference contrast image, by means of a transmitted-light technique. Each cycle is terminated with this recording of an image of the specifically labelled tissue specimen or the specifically labelled cell.

In this manner it is possible it obtain images of a random number of individual labelling patterns in the respective sample, cell or tissue specimen under examination through repeated labelling-imaging-bleaching cycles and to determine the resulting complex combination patterns of individual or numerous molecule distributions and to randomly project them as it were as combinatorial patterns to the biological structure (of a cell for example). Image superimposition and image analysis may be automatically performed by special computers. Computer-aided image superimposition of images of single or multiple cells facilitates the detection or identification and evaluation in a rational manner, e.g. over night, of such complex molecular organisation forms in cells as in principle cannot be visually detected as structure-bound patterns anymore. This eliminates a longish evaluation process of the individual images, for example manual copies of patterns. Moreover, essential quantitative conclusions as to correlational molecular concentrations and topological relationships may only be a obtained by means of special algorithms. Furthermore, owing to the evaluation having been performed visually so far, it was likewise hardly possible to combine the individual images to give a total image or to analyze the highly complex combinatorial behaviour in entire cell systems.

By means of the method according to the invention, it has now become possible to specifically label a sample, cell or tissue specimen a random number of times using a random number of different reagent solutions. Thus essential steric obstacles are excluded, as can be shown by changing the order of the reagents in each random sample, since the respective labelling results all remain virtually consult. The reagents used in this embodiment of the invention comprise antibodies, lectins, nucleic acids, biotoxins, immunoglobuline-binding molecules (such as proteins) or other specific ligands such as fluorochromes or enzymes. Specially preferred are fluorescent antibodies or ligands, in particular fluorochrome-conjugated antibodies or ligands. The objects used in this embodiment may be single cells, plural cells, tissue sections or also molecules placed onto certain stages or carriers or contained in certain media (such as gels).

The following is a general description of the individual automated steps for labelling and measuring molecular classes in a cell or tissue specimen. However, the method according to the invention is not intended to be restricted to these steps in any way. The individual steps may be interchanged or left out, as required.

An object such as a cell (e.g. fixed cells, e.g. acetone fixed cells, sodium azide treated cells or living cells) has been placed onto a microscope stage. After the sample has been prepared by hand and placed onto the stage of the device, the following automated steps are performed:

1. Taking up a first incubation solution Y1 (one or several fluorochrome-conjugated reagents)
2. Pipetting said solution Y1 onto the object
3. Incubating the object with said solution Y1 at a certain temperature, e.g. room temperature
4. Removing said incubation solution Y1
5. Dripping a washing solution Z1, e.g. a buffer solution, onto the object once or several times
6. Removing said washing solution Z1
7. Recording the fluorescence distribution pattern (imaging) (in the case of several fluorochromes, selective fluorescence recording filters are used for the imaging operation)
8. Pipetting a washing solution Z2 onto the object
9. Bleaching the sample by means of fluorescence excitation.
10. Absence of any more fluorescence will terminate the bleaching process. This point in time will be specified on the basis of previous tests or will be verified or determined by the imaging system.
11. Removing said washing solution Z2
12. Taking up a second incubation solution Y2 (containing one or several fluorochrome-conjugated reagents)
13. Dripping said solution onto the same cell sample (as above, without touching it or without having shifted its position)
14. Continuing as in above items 4–11. Subsequently repeating the same method using a 3rd, 4th, 5th, . . . Nth incubation solution.

Each cycle is terminated with the recording of a corresponding phase contrast image or a differential interference contract image. Steps 1–14 are all performed automatically. By means of computer-assisted image superimposition, the individual images are combined to give a total image, and then evaluated. This total molecular image of an individual cell or tissue specimen will give an insight into the complex molecular form of organisation in cells which basically cannot be visually determined or identified or evaluated if their number is as high as e.g. 18 different registered molecular classes since a number of $2^{18}$ different combinations will result in the case of the example mentioned. This differentiation resolution can readily be increased further. The known methods for the combinatorial analysis of systems, in particular of cellular systems, are strictly limited in view of their combinatorial differentiation capacity of between $2^3$ and $2^5$ at the most. Higher forms of molecular organisation resulting from combinations cannot be detected by means of the known methods.

In contrast to all known methods for a combinatorial analysis of system, in particular of cellular systems, the method according to the invention exhibits a considerably improved capacity for differentiating combined molecules (resolution capacity).

The method according to the invention allows detection of specific combinatorial differentiation spectra in the immune system from a single blood specimen alone.

Consequently, the method according to the invention makes it possible, in particular in biology and in medicine, to gain an insight into the molecular arrangement or the molecular distribution of individual molecular groups as well as an insight into specific disease symptoms and their possible treatments.

Practical use of the method has for example already shown that abnormal molecular combinations exist on cellular surfaces of cells of the immune system due to the virtually unlimited "resolution" for combinatorial molecular differentiation (i.e. differentiation resolution). These give completely new insights into abnormal surface codings for cell invasions, e.g. in the case of certain neurodegenerative diseases, and thus also into new ways of diagnosis and therapy.

A further application field for the method of the invention may be the mapping of complex genetic patterns, e.g. on gene chips, which will be highly significant in the future for multi drug testing or the detection of complex mutation patterns.

However, the process of the invention is particularly suited for determining or identifying and examining molecular organisation forms in a cell or tissuesample, without, however, being limited thereto.

In general, the object in liquid or solid form may be examined for its molecular structure or arrangement or the presence of molecular parts therein. Examples are the examination and determination or identification of molecular arrangements and combinations in semiconductors, alloys or plastics.

The following embodiment is intended to explain the invention in more detail, without limiting it.

Embodiment 18 different molecular classes in an accumulation of individual cells (isolated mononuclear blood leucocytes, applied to an object slide), i.e. in one and the same sample, are labelled by means of automatically controlled repeated incubation-imaging-bleaching cycles (RIIBC).

Preparation:
1. A cover glass is coated with the isolated cells.
2. Air-drying of the cells, approx. 10 min at room temperature (RT)
3. Short fixing thereof for 10 s in acetone (at RT)
4. Short air-drying thereof
5. Instant shock freezing of cover glass over precooled isopentane in liquid nitrogen
6. (long-term storage at minus 80 degrees) or
7. Dehydrating in acetone at minus 20 degrees for 20 min.
8. Air drying at RT
9. Rehydrating in PBS (phosphate buffered saline, pH 7.4)
10. Preincubating with 1:30 normal goat serum
11. Washing in PBS
12. Instantly placing cover glass onto a special carrier on the stage of the inverse microscope.
13. Focussing on the desired cells using a phase contrast lens, at the same time monitoring-the cells visually through the cellular.
14. Closing the humid chamber of the microscope stage.
15. Switching on pipetting robot
16. Entering the order and time intervals for the pipetting-imaging-bleaching steps into the computer
17. Filling reagents (antibody solutions, buffers) into the given vessels (e.g. Eppendorf reaction vessels) in the rack of the automatic machine.

Performing the RIIBC by means of the automatic machine:

Cycle 1:
1. A solution A (100 ml of solution, consisting of 80 ml of phosphate buffered saline, pH 7.4, +10 ml of fluroescein-isothiocyanate (FITC) coupled monoclonal antibodies-1, +10 ml of phycoerythrine (PE) coupled monoclonal antibodies-2) is taken up from a vessel containing said solution A by the pipetting robot. The vessel is a plastic reaction vessel.
2. The pipetting robot applies the solution A to the object (cells on the cover glass) resting on the object stage of the microscope.
3. The solution A is left to act on the object for a certain time (e.g. 20 min at room temperature).
4. Immediately following step 3, the pipetting robot sucks off this incubation solution and discards it or optionally pipettes it into a special discharge vessel (reaction vessel) in the rack of the automatic machine.
5. This is followed by 10 consecutive washing steps with buffer solutions which are sequentially taken up by the pipetting robot from reaction vessels in the rack, applied to the cell sample and subsequently sucked off again and discarded. Duration of the individual washing steps: approx. 2 min.
6. The 10 washing steps having been terminated, a buffer solution is again applied to the sample.
7. Immediately following step 6, an image is automatically taken in the phase contrast modus for a certain time by means of the imaging device (e.g. a CCD camera) over a certain period of time, and stored. Imaging occurs in several Z planes throughout the preparation in order to determine the optimum focussing plane by means of algorithms.
8. Immediately following step 7, the fluorescence shutter is opened and the fluorescence signal emanating from the fluorochrome phycoerythrine is recorded. The appropriate fluorescence filter data in the microscope need to be chosen such that a virtually total separation of PE and FITC is possible: e.g. emission filters for PE (DEPIL 575±7 nm) and for FITC (BP 515–545 nm). Imaging occurs separately for each of the two fluorescence signals for randomly programmable times (depending on the cell sample) or optionally simultaneously by means of dichroic filters. After a defined image recording time, the fluorescence shutter is closed again.
9. After step 8 the sample is bleached by leaving the fluorescence shutter open and exciting the sample by means of the excitation wavelength (soft bleaching of this kind will destroy the bound fluorochromes, but will save the properties of the immunogenic domains).
10. Once the bleaching time has elapsed, the fluorescence shutter is opened again automatically and a signal is recorded by the imaging device for each individual fluorochrome for the same time as above (this signal recording will provide an indication as to whether the bleaching time was sufficient to completely eliminate the emission signal: this is either decided upon by the software of the automatic machine, or respective fixed times are previously programmed for this method).

Cycle 2:
11. After step 10, the buffer solution is sucked off by the pipetting robot and a solution B (consisting of 80 ml of buffer +10 ml of FITC-coupled monoclonal antibodies-3+10 ml of PE-coupled antibodies-4) is applied to the object.
12. Step 11 is followed by the same steps as above (2 to 10: cycle 2).

Cycle 3:
13. The termination of cycle 2 is logically followed by cycle 3 with a new solution C (for further 2 antibodies of specificity 5 and 6, each coupled to FITC and PE, resp.).

Following cycle 3, further N cycles for a virtually random number of different antibodies may be run automatically without impairing the specificity of the labelling.

This principle will leave the antibodies,. with the coupled fluorochromes destroyed by bleaching, bound to the cells, while the cells are loaded again and again with new fluorochrome-coupled antibodies at the corresponding specific coupling sites. No steric obstacles occur in these couplings: this may be shown by changing the order of the antibody reactions in each random approach.

Thus a virtually random high number of molecular classes may be detected in individual cells in this manner. This provides a way of systematically examining the molecular combinations in cells.

What is claimed is:

1. An automated method for determining or identifying molecular classes, molecular groups or molecular parts in one and the same solid or liquid object, wherein said method comprises the step of examining and measuring a random number $X_n$ ($n=2, 3, \ldots N$) of molecular classes, molecular groups or molecular parts in said object through simultaneous or sequential application of a random number of reagent solutions $Y_n$ ($n=1,2,3, \ldots N$) wherein said method further comprises the automated steps of:

I. Taking up a first solution Y1 from a vessel containing said solution;

II. Applying said solution to said object resting on an object carrier means;

III. Leaving the solution to act on said object for an automatically adjusted period of time;

IV. Recording an image or signal distribution patterns of said object previously treated with the first solution Y1 or, alternatively, performing step V prior to step IV;

V. Removing solution Y1 from said object carrier means;

VI. Repeating steps I to V by repeatedly applying the first solution Y1 or a second solution Y2 or a mixture of first and second solutions to said object;

VII. Repeating steps I to VI with a random number of solutions Yn (n=1,2,3, . . . N) or a mixture thereof; and wherein the images or signal distribution patterns obtained in each cycle are recorded and transformed into a complex total image of the object to be examined by means of computer-aided image superimposition.

2. The automated method as claimed in claim 1 comprising bleaching cycles which may be repeated a random number of times.

3. The automated method as claimed in claim 1, wherein a washing solution Z1 or Z2 or Zn (n=1,2,3, . . . N) is applied to the object immediately or after a determined period, which may be varied, following the removal of the first or second solutions or solution Yn or a mixture thereof in step V.

4. The automated method as claimed in claim 1, wherein washing solutions Z1 to Zn (n=1,2,3, . . . N) are applied to said object in a specified order, which may be varied, immediately or after a determined period, which may be varied, following the removal of the first solution Y1 or the second solution Y2 or solution Yn or a mixture thereof in step V.

5. The automated method as claimed in claim 1, wherein said solutions comprise colorants, complexing agents, antibodies or ligands.

6. The automated method as claimed in claim 1, said object being a sample, a tissue specimen, or one or plural cells.

7. The automated method as claimed in claim 6, wherein in said sample, said tissue specimen, or said one or plural cells, a random number Xn (n=2,3, . . . N) of molecular classes, molecular groups or molecular parts are examined and determined or identified by means of a single reagent solution.

8. The automated method as claimed in claim 6, wherein in said sample, tissue specimen, or said one or plural cells, a random number Xn (n=2, 3 . . . N) of molecular classes or molecular groups are examined and determined or identified by means of at least two different reagent solutions Yn and Yn+x in a specified order which may be varied.

9. The automated method as claimed in claim 1, said reagent solution comprising fluorochrome-conjugated antibodies or ligands.

10. The automated method as claimed in claim 1, comprising the following automatic steps:

I. Taking up a first fluorochrome-containing reagent solution Y1, from a vessel and pipetting said solution onto a sample, a tissue specimen, or one or plural cells;

II. Incubating said sample, said tissue specimen, or said one or plural cells over a certain period of time;

III. Removing said reagent solution Y1, pipetting a washing solution Z1 to Zn onto the object at least once;

IV. Recording the signal distribution pattern of said sample, said tissue specimen, or said one or plural cells;

V. Bleaching said sample, said tissue specimen, or said one or plural cells until no fluorescence is left to be detected;

VI. Taking up a second reagent solution;

VII. Repeating steps I to VI with a random number of reagent solutions Yn or mixtures thereof.

11. The automated method as claimed in claim 1, using an automated device for determining or identifying molecular classes, molecular groups and molecular parts in one and the same liquid or solid object, said device comprising a combination of a pipetting system, a 3D handling system and an optical measuring system, said pipetting system, said 3D handling system and said optical measuring system being controlled and monitored by a computer, and said pipetting system providing for automatic pipetting for taking up and dispensing liquids, for automatic pipette change, and and said pipetting system exhibiting an accuracy in repeatedly positioning the pipette, which is at least ±0.1 mm.

12. The automated method as claimed in claim 11, wherein said device is equipped with an imaging device.

13. The automated method as claimed in claim 11, wherein said 3D handling system is capable of reciprocating said pipetting system with a predetermined accuracy of repeatedly positioning the pipette.

14. The automated method as claimed in claim 11, wherein said optical measuring system comprises an inverse or upright microscope stand.

15. The automated method as claimed in claim 14, wherein said microscope stand includes a climatic box.

16. The automated method as claimed in claim 11, wherein said 3D handling system comprises a robot or linear guiding system.

17. The automated method as claimed in claims 11, wherein said device records images of a random number of individual labelling patterns of one and the same object under examination, transforming them into a molecular combination pattern by means of computer assisted image superimposition.

* * * * *